United States Patent
Bregulla et al.

(10) Patent No.: US 10,806,616 B2
(45) Date of Patent: Oct. 20, 2020

(54) DOUBLE BALLOON

(71) Applicant: Bentley InnoMed GmbH, Hechingen (DE)

(72) Inventors: Rainer Bregulla, Balingen (DE); Milisav Obradovic, Lorrach (DE)

(73) Assignee: Bentley InnoMed GmbH, Hechingen (DE)

( * ) Notice: Subject to any disclaimer, the term of this patent is extended or adjusted under 35 U.S.C. 154(b) by 147 days.

(21) Appl. No.: 15/571,384

(22) PCT Filed: May 6, 2016

(86) PCT No.: PCT/EP2016/060200
§ 371 (c)(1),
(2) Date: Nov. 2, 2017

(87) PCT Pub. No.: WO2016/177885
PCT Pub. Date: Nov. 10, 2016

(65) Prior Publication Data
US 2018/0303645 A1   Oct. 25, 2018

(30) Foreign Application Priority Data
May 6, 2015   (DE) .......... 10 2015 107 038

(51) Int. Cl.
*A61F 2/958*   (2013.01)
*A61F 2/954*   (2013.01)
*A61M 25/10*   (2013.01)

(52) U.S. Cl.
CPC .............. *A61F 2/958* (2013.01); *A61F 2/954* (2013.01); *A61M 25/1011* (2013.01);
(Continued)

(58) Field of Classification Search
CPC .......... A61F 2/958; A61M 2025/1013; A61M 2025/1059; A61M 2025/1061;
(Continued)

(56) References Cited

U.S. PATENT DOCUMENTS 5,049,132 A   9/1991  Shaffer et al.
5,536,252 A * 7/1996  Imran ................ A61M 25/1011
                                                    604/101.02
(Continued)

FOREIGN PATENT DOCUMENTS

EP    0835673 A2   4/1998
EP    2848279 A1   3/2015
(Continued)

OTHER PUBLICATIONS

Chinese Office Action dated Sep. 12, 2019 issued in connection with CN201680026360.6.
(Continued)

*Primary Examiner* — Ryan J. Severson
(74) *Attorney, Agent, or Firm* — Brooks Kushman P.C.

(57) ABSTRACT

The invention relates to a balloon catheter, in particular for the widening of stents in fenestrations, being provided with a first inner balloon (4), a second outer balloon (5), with said second balloon (5) completely enclosing the first balloon (4), separate supply lines in the catheter (2) leading to the first (4) and second balloon (5), which allow the balloons (4, 5) to be pressurized independently of one another, a central lumen (3) for a guidewire, wherein in the expanded state, both balloons (4, 5) in the proximal region (P) have a diameter which is enlarged in relation to that of the distal region (D).

15 Claims, 5 Drawing Sheets

(52) U.S. Cl.
CPC .. *A61F 2250/0039* (2013.01); *A61M 25/1002* (2013.01); *A61M 2025/1013* (2013.01); *A61M 2025/1045* (2013.01)

(58) Field of Classification Search
CPC ...... A61M 2025/1072; A61M 25/1002; A61M 25/1011
See application file for complete search history.

(56) References Cited

U.S. PATENT DOCUMENTS

| | | | | | |
|---|---|---|---|---|---|
| 5,632,762 | A | * | 5/1997 | Myler | A61F 2/90 606/192 |
| 6,605,056 | B2 | * | 8/2003 | Eidenschink | A61M 25/104 604/101.01 |
| 6,733,474 | B2 | * | 5/2004 | Kusleika | A61M 25/1011 604/101.02 |
| 8,034,022 | B2 | * | 10/2011 | Boatman | A61M 25/1011 604/101.01 |
| 8,182,446 | B2 | * | 5/2012 | Schaeffer | A61M 25/10 604/101.02 |
| 8,317,747 | B2 | * | 11/2012 | Kusleika | A61M 25/1011 604/101.01 |
| 8,591,461 | B2 | * | 11/2013 | Boatman | A61M 25/1011 604/101.01 |
| 8,784,602 | B2 | * | 7/2014 | Schaeffer | A61M 25/10 156/293 |
| 8,911,399 | B2 | * | 12/2014 | Boatman | A61M 25/1011 604/101.01 |
| 9,034,025 | B2 | * | 5/2015 | Sanati | A61F 2/954 623/1.11 |
| 9,174,030 | B2 | * | 11/2015 | Boatman | A61M 25/1011 |
| 9,956,384 | B2 | * | 5/2018 | Charlebois | A61M 25/0155 |
| 9,968,470 | B2 | * | 5/2018 | Plowiecki | A61F 2/856 |
| 10,004,622 | B2 | * | 6/2018 | Sanati | A61F 2/954 |
| 2002/0032406 | A1 | * | 3/2002 | Kusleika | A61M 25/1011 604/101.02 |
| 2004/0260239 | A1 | * | 12/2004 | Kusleika | A61M 25/1011 604/101.02 |
| 2006/0258981 | A1 | * | 11/2006 | Eidenschink | A61M 25/104 604/103.1 |
| 2013/0060216 | A1 | | 3/2013 | Archimedes et al. | |
| 2013/0060316 | A1 | * | 3/2013 | Sanati | A61F 2/954 623/1.11 |
| 2013/0338761 | A1 | | 12/2013 | Plowiecki et al. | |
| 2015/0039073 | A1 | * | 2/2015 | Plowiecki | A61F 2/856 623/1.11 |
| 2015/0081006 | A1 | * | 3/2015 | Chuter | A61F 2/958 623/1.11 |
| 2015/0209558 | A1 | * | 7/2015 | Charlebois | A61M 25/0155 604/101.02 |
| 2015/0245935 | A1 | * | 9/2015 | Sanati | A61F 2/954 623/1.11 |
| 2018/0221630 | A1 | * | 8/2018 | Obradovic | A61F 2/958 |
| 2018/0303645 | A1 | * | 10/2018 | Bregulla | A61F 2/954 |

FOREIGN PATENT DOCUMENTS

| | | |
|---|---|---|
| JP | 2008541872 | 11/2008 |
| RU | 86475 U1 | 9/2009 |
| RU | 2491038 C2 | 8/2013 |
| SU | 1604380 A1 | 11/1990 |
| WO | WO 96/13298 A1 | 5/1996 |
| WO | WO96/13298 A1 | 5/1996 |
| WO | WO 97/17101 A1 | 5/1997 |
| WO | WO 2006/116495 A1 | 11/2006 |
| WO | WO2014/122757 A1 | 8/2014 |

OTHER PUBLICATIONS

Russian Office Action dated Aug. 29, 2019 issued in connection with RU2017142354.
Russian Office Action dated Aug. 29, 2019 issued in connection with RU2017142354. (German translation).
Office Action dated Apr. 29, 2020 in connection with related Indian Patent Appl. No. 201747039455.
Japanese Office Action dated Feb. 28, 2020 issued in related Japanese Patent Appl. No. 2017-5589003.

* cited by examiner

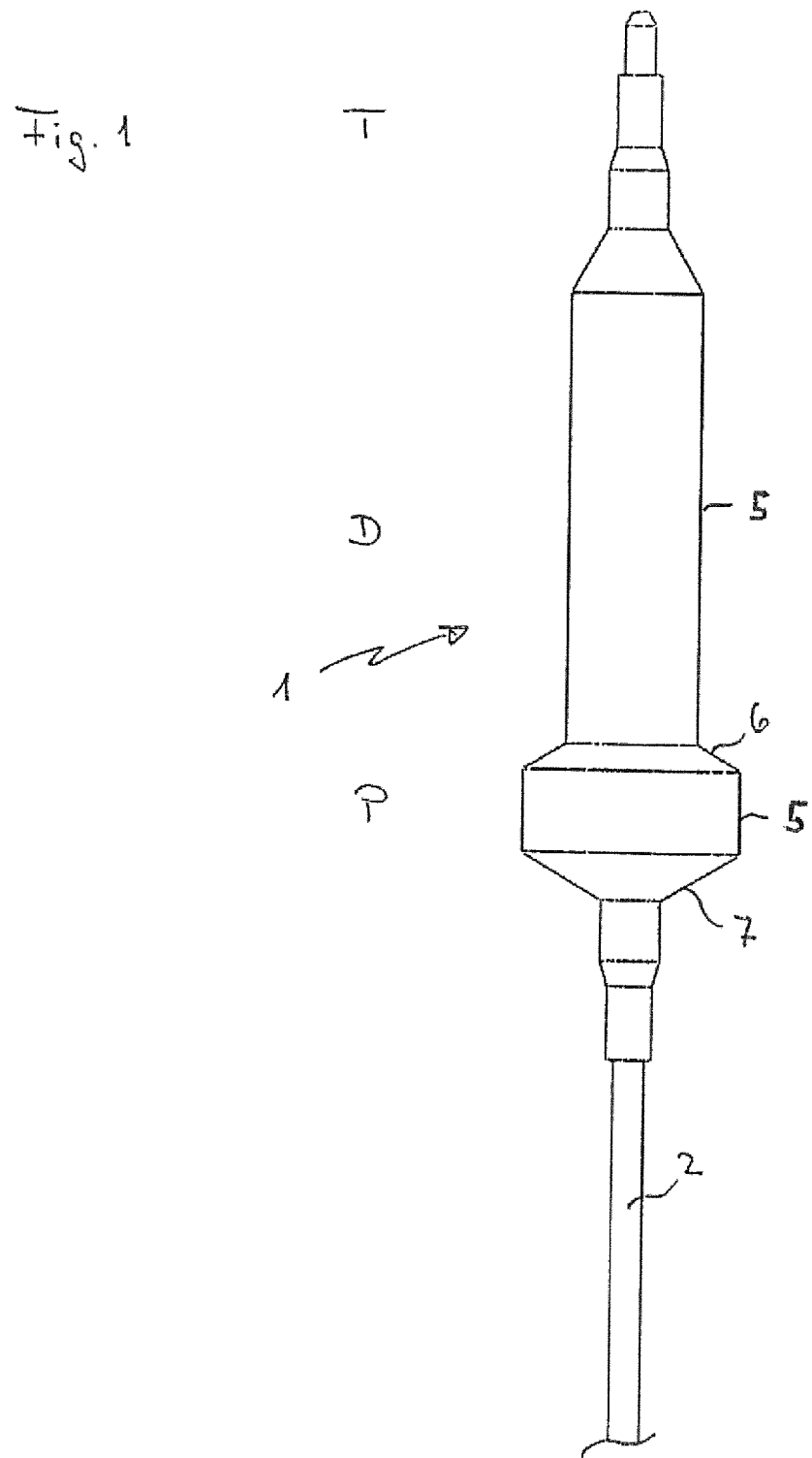

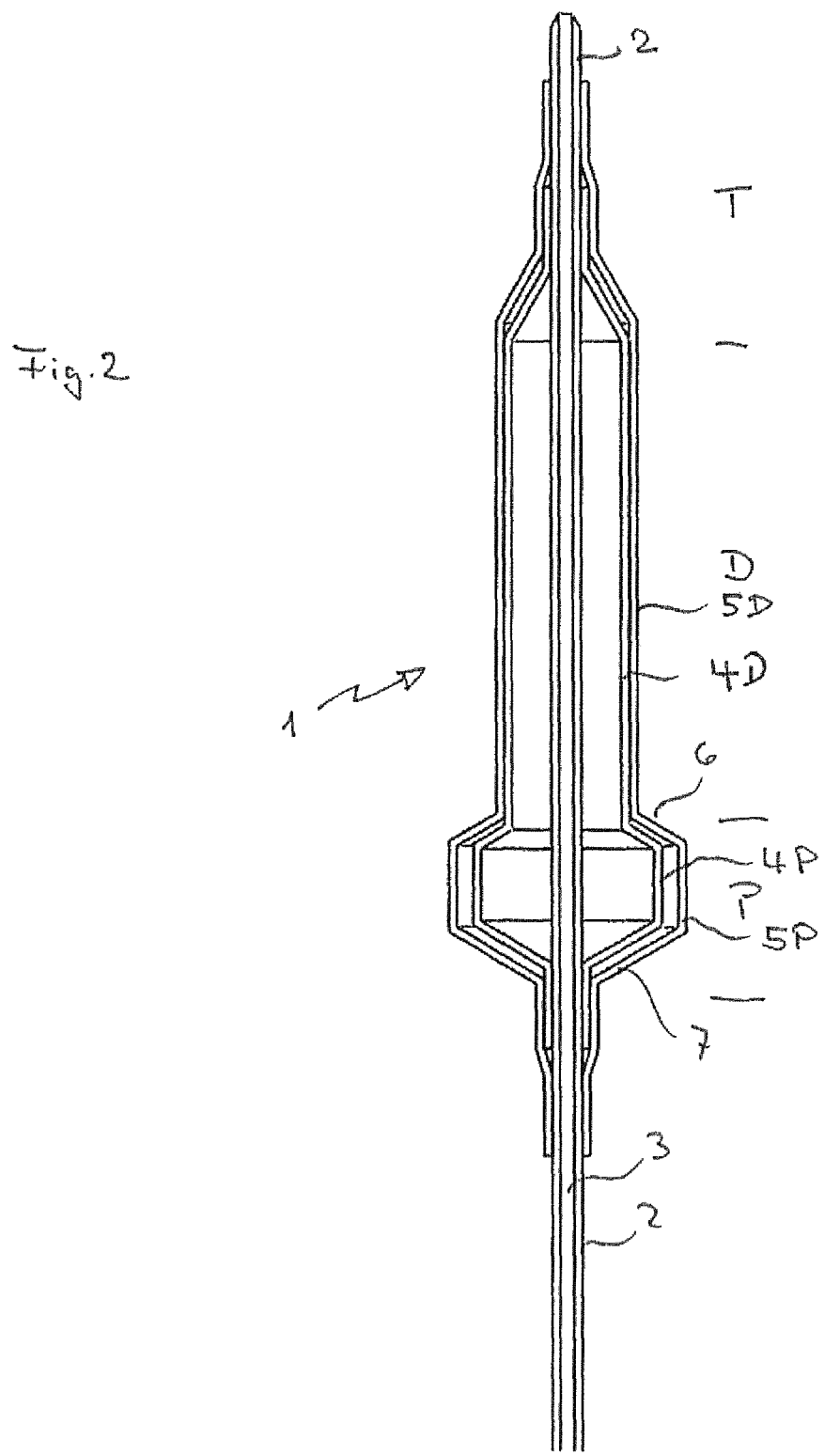

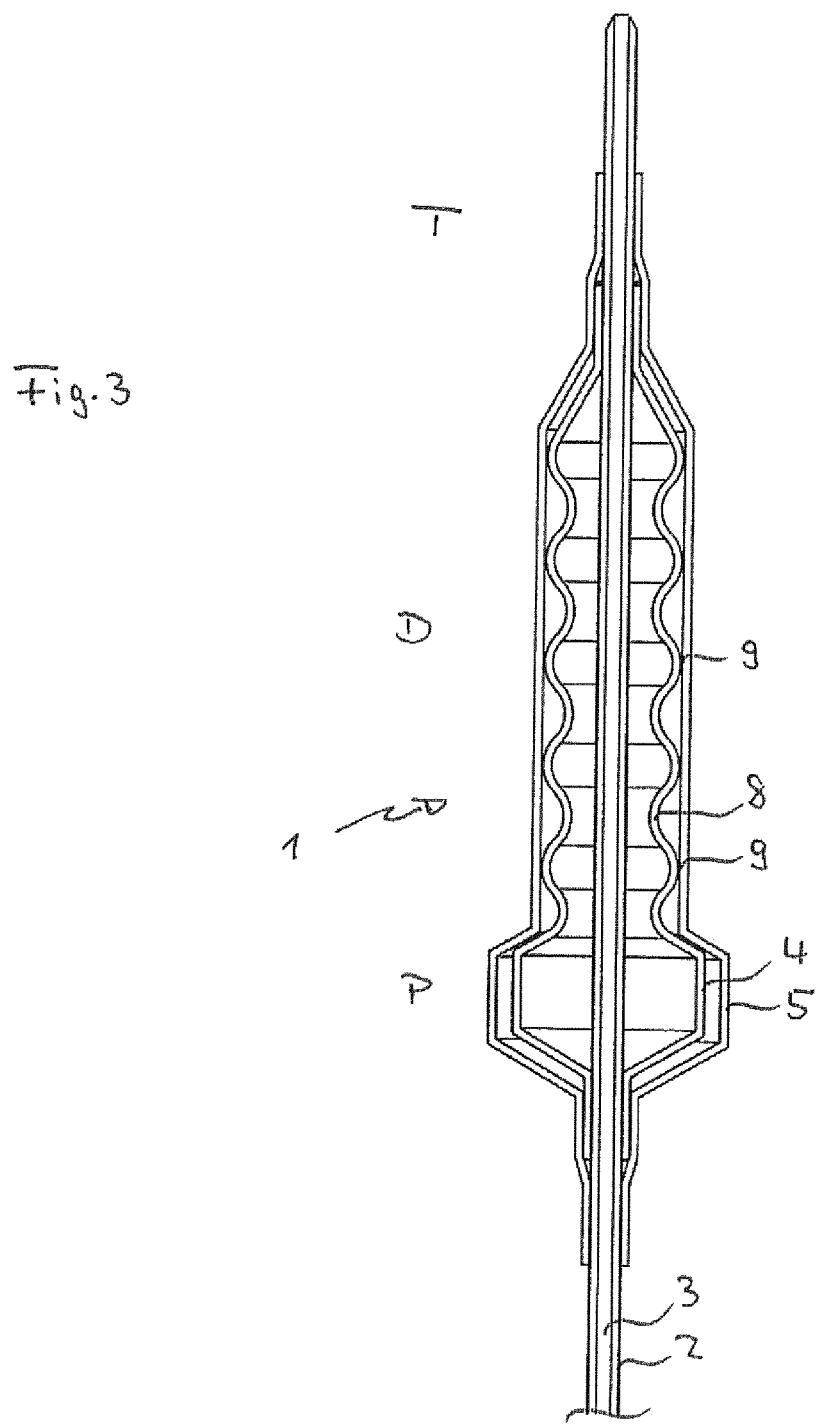

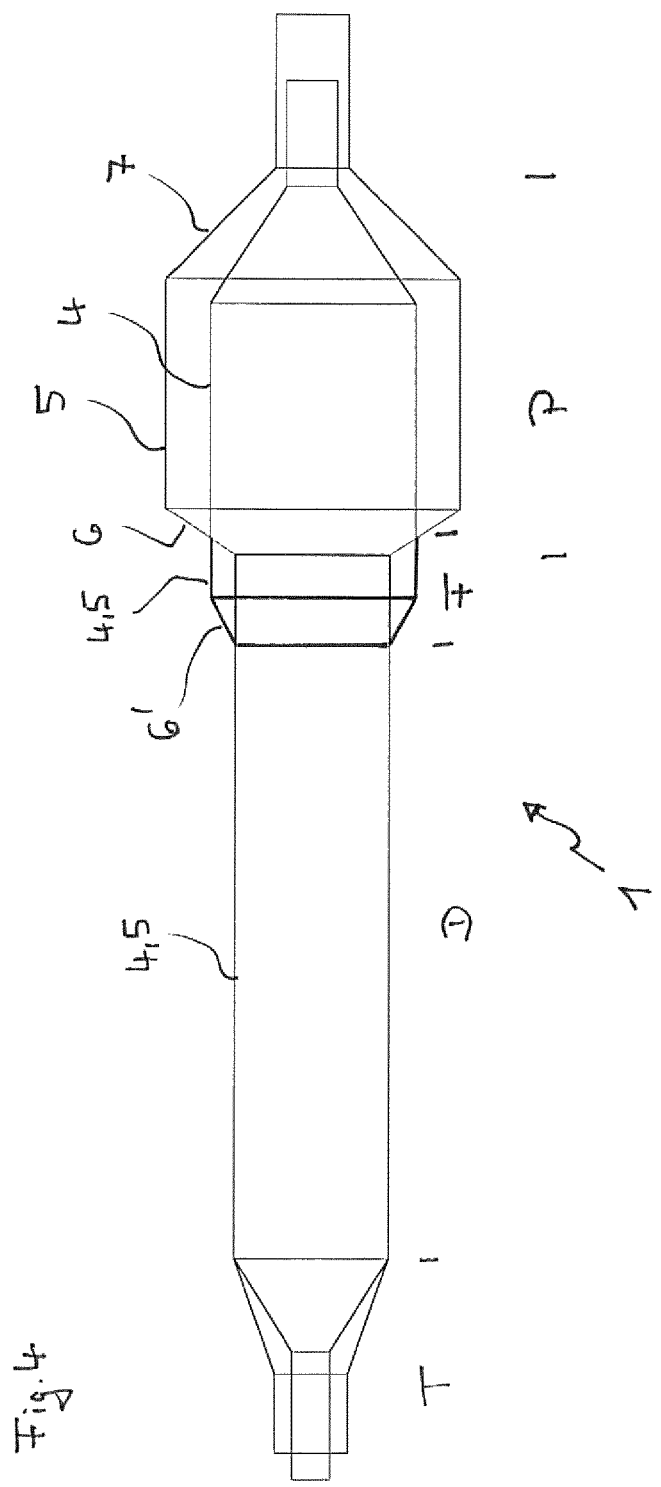

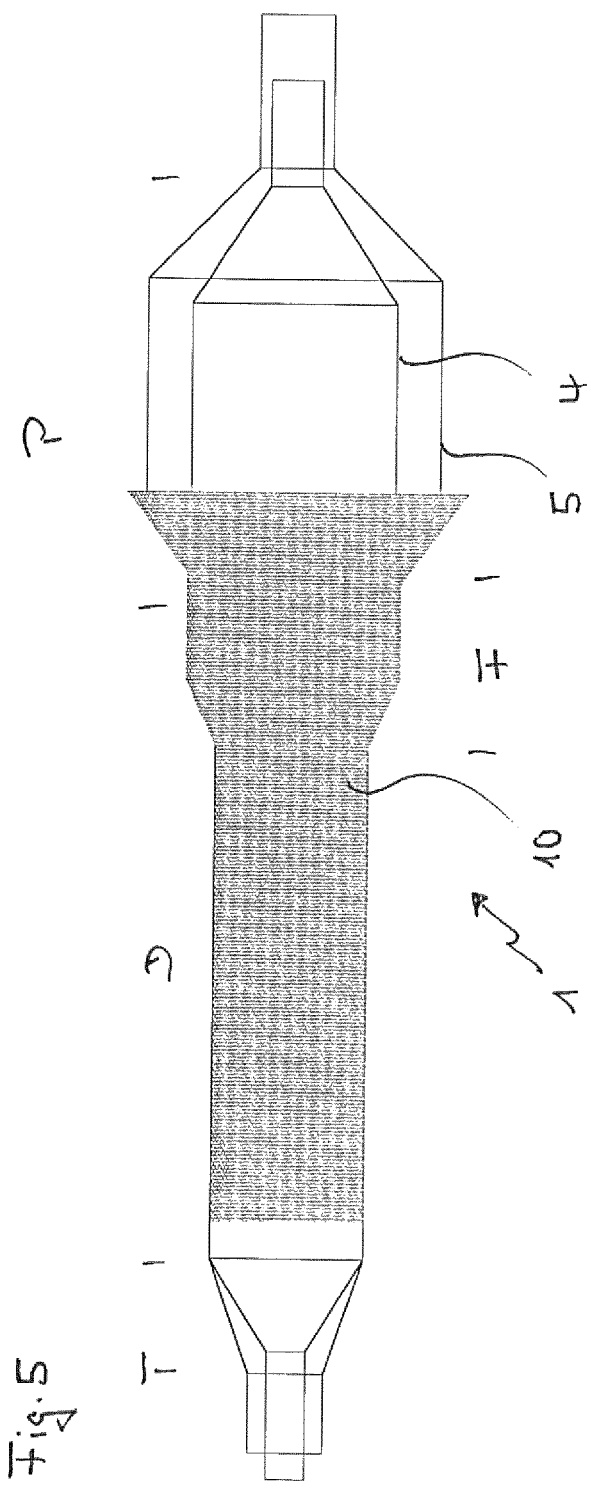

DOUBLE BALLOON

The invention relates to a balloon catheter, particularly for the widening of stents in fenestrations, with a first inner balloon, a second outer balloon, separate supply lines in the catheter to the first and second balloon, which allow the balloons to be pressurized independently of each other, a central lumen for a guidewire, with the second balloon completely enclosing the first balloon.

Balloon catheters have been used for many years to widen stents in vessels. For the purpose of widening stents, a stent is crimped onto the balloon catheter and dilated and placed at the desired implantation site with the help of a balloon catheter. Following this, the balloon catheter is removed from the vessel without the stent.

In angioplasty, balloon catheters are used for widening a narrowed vessel mechanically and press plaques that have formed there against the vessel wall.

A special problem arises when, aside from the main branch, also the branching vessel must be provided with a stent in the area of vascular bifurcations. In this case, a stent fitted with a fenestration is first arranged in the main branch, where it is implanted in such a way that the window is positioned in the area of the junction. Afterwards, another stent is inserted into the branching off vessel, dilated there and adapted to the stent arranged in the main branch by widening. As a rule, this requires several separate steps, in particular if the branching off vessel narrows in its course and a gradual widening has to be accomplished. In addition, the stent in the side branch has to be adjusted and matched to suit the window and the stent configuration in the main branch.

For this adjustment it is possible to proceed in steps using several balloons of different diameters. However, a so-called "balloon in the balloon" may also be employed, in which two balloons are coupled to each other in such a way that they can be pressurized separately and be used to achieve different expansion volumes. A disadvantage in this context is the effort involved when using several separate balloons and the fact that the coupled balloons are difficult to adapt.

It is thus the objective of the present invention to provide a balloon catheter by means of which stents can be placed in branching vessels and connected to a stent having a fenestration placed in the main branch.

This objective is achieved by proposing a balloon catheter of the kind first mentioned above, wherein the two balloons in expanded state have a diameter in the proximal area that is larger than in the distal area.

The balloon catheter proposed by the invention consists of a first inner balloon and a second outer balloon that completely encloses the inner balloon. Both balloons are provided with separate supply lines so that they can be dilated independently of each other. As a rule, the inner balloon is dilated first with a view to placing a stent in a side branch by means of the proximal end of the balloon structure, followed by the separate dilation of the second outer balloon to widen this stent in the entry area to assume a trumpet-like shape.

The two balloons have a proximal and distal area, with the distal area being of slimmer configuration. It can have an even diameter over its length, but may also become narrower towards the distal end of the catheter to allow adaptation to narrowing side branches.

The proximal area of the balloons in the balloon catheter proposed by the invention has a diameter that is considerably larger than in the distal area. In particular, the diameter is increased by about 50 to 100%.

Usually, the inner balloon has a diameter (in expanded state) of 5 to 8 mm in the proximal region, while the diameter of the outer balloon ranges between 8 and 14 mm.

The inventive balloon catheter can have a graduation within the balloons that as well extends from a large diameter in the proximal area to a small diameter in the distal area or terminal area.

The proximally enlarged area of the balloons shows a relatively steep rise on its flanks that, preferably, is evenly formed on both sides, i.e. the rise of the catheter shaft on the one hand and the rise of the proximal part of the balloons on the other hand. Expediently, the rise or increase ranges between 45 and 75 in relation to the axis of the catheter. A steep rise in the enlarged zone is to be seen positive for the trumpet-like widening of the stent in the entry area of the branching vessel and conducive to the adaptation to the stent placed in the main branch.

The first or inner balloon abuts directly on the inner wall of the second balloon in the distal area and is expediently connected to it, for example by welding. Consequently, the expansion of the first balloon results in a very precise widening only to the desired extent, and an expansion of the second balloon does not affect the distal area. In the proximal region, the first or inner balloon has a considerably smaller diameter than the second outer balloon and is not connected to it. This means that the second outer balloon can be dilated individually and is thus capable of being widened to a diameter that is significantly larger than that of the first balloon. This is very conducive to the widening of the stent in the entry area of the vessel branching. At the same time, however, the first inner balloon in the first phase of widening is already capable of pre-dilating also the entry area of the stent to a certain extent; the "fine adjustment" to the desired final dimension is then achieved by means of a separate dilatation of the second outer balloon. The reverse order, involving the widening of the stent in the proximal region in a first step and fine adjustment by means of the inner balloon in a second step, is an alternative to this.

According to a preferred variant, the inner balloon has a larger diameter than the outer balloon in the transitional area from the proximal to the distal zone, so that the widening of said inner balloon in a second step causes the outer balloon to be additionally expanded in this area. For this purpose, the inner balloon may be expanded by 25 to 40% in diameter compared to the distal area.

In the distal area, the first balloon may be welded to the outer balloon in places only, which results in a better adaptation to irregularities in the vessel wall. In this case, however, a continuous weld seam is also necessary at the transition location from the proximal to the distal region in order to confine this expansion of the second balloon to the proximal region.

According to a special embodiment, the first inner balloon is designed so as to be wave-shaped in the distal area thus reaches the inner wall of the outer balloon at certain points and is welded to it in this area. This also allows the stent to be excellently adapted to the vessel surface of the branch to be dilated. The depressions permit the pressure to be well distributed and the balloon to be effectively adapted to narrowing vessel sections.

The balloon catheter proposed by the invention is manufactured and handled in the usual way. Also, the materials to be used are those commonly employed in this field. The difference to the state of the art solely concerns the design of the balloons.

For the balloons, materials that are commonly adopted for this purpose can be employed. Preferably, a material with limited extensibility (non-compliant) is used for the inner balloon, such as polyamide 12, PET, nylon, and for the outer balloon a well extensible (compliant or semi-compliant) material such as silicone rubber, Pebax, PA 11 or a mixture of Pebax and PA 11.

The invention is explained in more detail by way of the enclosed figures, where

FIG. 1: shows an overall view of a balloon catheter proposed by the invention;

FIG. 2: is a sectional view of the balloon catheter illustrated in FIG. 1;

FIG. 3: shows a second variant of an inventive balloon catheter as a sectional view:

FIG. 4: depicts a third variant of an inventive balloon catheter; and

FIG. 5: shows a balloon catheter as per FIG. 4 with crimped-on stent.

FIG. 1 shows an inventionally designed balloon catheter 1 with the distinctly widened proximal region P with steep flanks 7 extending towards the catheter and 6 towards distal region D, the relatively slender distal region D, which decreases in steps to the catheter diameter. The catheter 2 extends through the balloon structure 1 and terminates distally. The illustration shows the balloon catheter in an expanded state, with the contour being determined by the outer balloon 5. The inner balloon (which is not shown) supports outer balloon 5 in the significantly widened area P.

For use, a stent is crimped onto the balloon catheter, said stent being widened through the expansion of the balloons and placed in a blood vessel. The illustration shows catheter 1 in an expanded state.

FIG. 2 shows a sectional representation of the balloon catheter according to FIG. 1 with catheter 2, a free lumen 3 for a guidewire used to place the catheter in position, the inner balloon 4 and the outer balloon 5.

The double balloon is subdivided into the proximal area P, distal area D, and terminal area T.

The proximal region P is designed to be considerably wider than the distal region D, with the outer balloon 5 P having a larger diameter in this area than the inner balloon 4 P. In the distal area D, the inner balloon 4 D abuts directly on the inner wall of the outer balloon 5 D and is connected to it. This means that during the dilatation of the balloons, which can take place separately, the expanding inner balloon generally acts on and always takes the outer balloon with it. In the proximal region P, however, the outer balloon 5 P can be individually expanded via a separate channel and expands to a greater extent than the inner balloon 4 P in this region, which enables a trumpet-like widening and adaptation of an already placed side branch stent to be produced in the branching area.

In the terminal area T, both balloons slim down and seal off tightly before the end of catheter 2. The channels which serve to fill the balloons with fluid are conventional and not shown in the drawing.

FIG. 3 shows a variant of the double balloon according to the invention, where the outer balloon has the shape as defined in FIGS. 1 and 2, while a wavelike configuration has been provided for the inner balloon, i.e. comprising drawn-in portion 8. These drawn-in portions result in creating a clearance to the wall of the outer balloon 5, which means that in this area the pressure that is exerted on a stent during dilatation is lower than in the peak areas 9. The inner balloon 4 is welded to the outer balloon 5 at peak areas 9.

It goes without saying that there are numerous variations in the design of the proximal and distal areas. According to one variant, the proximal region has a more spherical shape. The distal areas are shown to have the same diameter, but it is of course also possible to provide for a further graduation or slimming towards the terminal end of the catheter. For example, the diameter of the distal area can be reduced by 40% over its length towards the terminal end, and this slimming down can be brought about continuously or in steps.

FIG. 4 shows a variant of the inventive double balloon, in which the two balloons 4 and 5 are shown fully expanded. The representation is again divided into a proximal, distal and terminal region, with the proximal region P being greatly widened in comparison to the distal region D. The outer contour of the double balloon in the proximal region P is predominantly determined by the outer balloon 5, with the exception of the transitional area F adjacent to distal region D where the more greatly expanded inner balloon 4 causes the outer contour to be widened in the region of the transition F. Area F with flank 6' is essentially determined by the expanded inner balloon 4. Otherwise, the reference numerals coincide with those indicated in FIGS. 1 to 3.

During application, a stent crimped onto the double balloon 1 is first expanded with the help of the outer balloon 5. This results in a trumpet-shaped widening of the proximal region of the stent in the zone where the stent is introduced into the branch exiting the main vessel. In a second step, the inner balloon 4 is then expanded which leads to a further widening in the transition area F and causes the crimped-on stent to be secured to the vessel wall in this area. The contour shown in bold in the representation of transition area F makes it clear to what an extent the inner balloon 4 is expanded in this area by the outer balloon 5, A second flank 6 and a stepped transition towards distal area D is thus created.

FIG. 5 is a representation of the balloon catheter 1 with crimped-on stent 10 which in comparison to area D is additionally widened in the transition area F by the effect of the inner balloon 4. This enables an optimal integration to be achieved into the entry zone of a branching vessel and the fixation in this branching vessel in the entry area.

The invention claimed is:

1. Balloon catheter, in particular for the widening of stents in fenestrations, having a proximal region, a distal region, and a terminal region, the proximal region provided with a first inner balloon, a second outer balloon, said second balloon completely enclosing the first balloon, the terminal region being where both balloons slim down and seal off tightly before the end of the catheter, the distal region being distal to the proximal region and proximal to the terminal region so as to be between the proximal region and the terminal region, separate supply lines in the catheter leading to the first and second balloon, which allow the balloons to be pressurized independently of one another to an enlarged, expanded state, a central lumen for a guidewire, wherein in the expanded state, both balloons in the proximal region have a diameter which is enlarged in relation to the distal region and the first balloon is directly connected to at least part of the second balloon in the distal region.

2. Balloon catheter according to claim 1 wherein the balloons are provided with a graduation or steplike configuration.

3. Balloon catheter according to claim 1 wherein the proximal region of both balloons is expanded by 30% to 100% relative to the distal region.

4. Balloon catheter according to claim 1 wherein the enlarged proximal region has rising flanks.

5. Balloon catheter according to claim 4 wherein the rise of the flanks ranges between 45 and 75° relative to the catheter axis.

6. Balloon catheter according to claim 4 wherein the rise of the flanks is uniform on both sides of the proximal region.

7. Balloon catheter according to claim 1 wherein in the expanded state, the inner balloon and the outer balloon each have a transition region between the proximal and distal region.

8. Balloon catheter according to claim 7 wherein the inner balloon is expanded in the transition region by 25% to 40% compared with the distal region.

9. Balloon catheter according to claim 7 with a crimped-on stent.

10. Balloon catheter according to claim 1 wherein a weld seam connects the first balloon to the second balloon in the distal region.

11. Balloon catheter according to claim 1 wherein a weld seam connects the first balloon to the second balloon over the entire length of distal region.

12. Balloon catheter according to claim 1 wherein the first balloon has spot weld seams connecting the distal region to the second balloon, with the proximal region of the second balloon being separated from the distal region of the second balloon by the spot weld seams.

13. Balloon catheter according to claim 12 wherein the first balloon has drawn-in portions in the distal region and peak areas, said spot weld seams connecting the first balloon to the second balloon at the peak areas.

14. Balloon catheter according to claim 12 with a crimped-on stent.

15. Balloon catheter according to claim 1 with a crimped-on stent.

\* \* \* \* \*